US005721136A

United States Patent [19]

Finney et al.

[11] Patent Number: 5,721,136

[45] Date of Patent: Feb. 24, 1998

[54] SEALING DEVICE FOR THERMAL CYCLING VESSELS

[75] Inventors: Michael J. Finney, Cambridge; Paul Titcomb, Waltham, both of Mass.

[73] Assignee: MJ Research, Inc., Watertown, Mass.

[21] Appl. No.: 337,160

[22] Filed: Nov. 9, 1994

[51] Int. Cl.$^{6}$ .............................. C12M 1/02; C12M 1/38

[52] U.S. Cl. .................................... 435/287.2; 435/288.1; 435/288.4; 435/305.3; 435/305.4; 428/66.3; 428/343; 428/351; 428/447; 220/526; 220/359

[58] Field of Search ............................ 435/286.1, 287.2, 435/288.1, 288.2, 288.4, 303.1, 305.1–305.4, 288.3; 422/99, 101, 102; 220/23.2, 23.4, 23.8, 23.83, 523, 526, 255, 359, 378; 100/54, 92, 211; 428/40, 163, 167, 172, 411.1, 446, 447, 450, 451, 465; 359/396, 398; 156/69

[56] References Cited

U.S. PATENT DOCUMENTS

| | | | |
|---|---|---|---|
| 2,691,935 | 10/1954 | Zeiler et al. | 100/211 |
| 3,843,764 | 10/1974 | Grawey et al. | 428/447 |
| 4,299,920 | 11/1981 | Peters | 435/288.4 |
| 4,318,490 | 3/1982 | Schneider | 156/69 |
| 4,402,911 | 9/1983 | Walters | 422/102 |
| 4,499,148 | 2/1985 | Goodale et al. | 156/272.6 |
| 4,728,567 | 3/1988 | Razzano et al. | 428/317.1 |
| 5,038,852 | 8/1991 | Johnson et al. | 165/12 |
| 5,056,427 | 10/1991 | Sakabe et al. | 100/211 |
| 5,123,477 | 6/1992 | Tyler | 165/2 |
| 5,192,503 | 3/1993 | McGrath et al. | 435/288.3 |
| 5,282,543 | 2/1994 | Picozza et al. | 422/99 |
| 5,342,581 | 8/1994 | Sanadi | 422/101 |
| 5,346,672 | 9/1994 | Stapleton et al. | 422/102 |
| 5,364,790 | 11/1994 | Atwood et al. | 435/288 |
| 5,482,591 | 1/1996 | Reo | 156/306.6 |

*Primary Examiner*—William H. Beisner
*Attorney, Agent, or Firm*—Wolf, Greenfield & Sacks, P.C.

[57] ABSTRACT

A sheet of material seals vessels for biochemical reactions which undergo thermal cycling, and comprises a multilayer composite sheet which is placed over the openings of one or more reaction vessels. The multilayer composite sheet material has at least two layers, one layer providing strength and integrity to the material and the second layer being relatively thick comprising a deformable substance with a tacky surface to contact and seal vessels for biochemical reactions.

14 Claims, 3 Drawing Sheets

SEALING DEVICE FOR THERMAL CYCLING VESSELS

BACKGROUND OF THE INVENTION

1. Field of the Invention

This invention pertains to thermal-cycling vessels and seals therefore to prevent cross contamination and escape of vapors from the thermal-cycling vessels.

2. Description of the Prior Art

For the efficient performance of analytical techniques such as the polymerase chain reaction, the ligase chain reaction, in situ versions of these techniques, and thermal cycle DNA sequencing, thermally cycling large numbers of biological samples simultaneously is essential. In the prior art, when large number of analyses were performed, individual reaction solutions are placed in the wells of a multiple-well vessel. Most commonly, in automation-compatible vessels known as "microplates", individual wells are arranged in a grid pattern with a unit spacing of 9 mm or integer fraction of 9 mm. In the past, it was known to form the microplates as a single unit, usually of a plastic material which has been formed to contain a number of wells in a XY matrix. In addition, in the prior art, microplates may be composed of individual vessels held in a 9 mm grid by a rack, temperature control block or other positioning apparatus which holds the vessels in an upright position with the vessel's open mouth at the top of the vessel. Alternatively, for performance of in situ techniques in the prior art, assays are conducted on biological samples, such as tissue sections or individual cells, that must be viewed with a microscope after the reaction is complete. Because of the fragility of these samples, it is highly preferable to perform the thermal cycling procedures with the samples already affixed to a microscope slide. While the temperature and the timing of a thermal cycling process may vary with the particular cycling instrument and the procedure to be performed, typically in all of the above mentioned analytical techniques, the aqueous analyte solution is thermally cycled from a low temperature of approximately 35° C. to 72° C. and to a high temperature which is normally 90° C. to 95° C. In a typical analysis, 20–50 thermal cycles between the lowest and highest temperature are performed. Without some form of a sealing device, the aqueous phase is quickly reduced in volume through the loss of water vapor. This changes the concentrations of reaction components and invalidates the test results.

The problem lies in providing a sealing device to form a gas-tight seal which also allows easy reopening for access to the reaction for further analysis. In addition, in certain of the above-mentioned analytical techniques, it is necessary to isolate the individual wells and prevent cross contamination of samples, so that use of a sealing device (placement or removal) must not lead to a splashing (when the sealing device is removed) or the formation of aerosols which might migrate from one well to another well and thus invalidate the test procedures. In the prior art, there are two known methods to seal multiple-well vessels, a sample contact method and a non-sample contact method. In a sample contact method, a sealing device is applied so that it directly contacts the reaction solution and thus eliminates or substantially reduces the vapor phase above the liquid reaction volume. This is most commonly accomplished by applying to the top surface of the reactions a small volume of oil, where the oil is chosen to be immiscible with water, less dense than water and non-volatile. Although the use of such oil is easy and effective, it is usually necessary to remove the oil before the reactions can be further analyzed during and after cycling. This takes time if done by hand, is difficult to automate and can result in contamination or cross contamination of samples. This technique is called a sample contact method because the sealing device, the oil, contacts the reaction volume of the sample.

Also in the prior art, for in situ techniques, sealing is accomplished by any of several sample-contact methods. Sample biological materials are fixed to a glass microscope slide and a liquid reaction mixture is applied thereto. A stiff glass or plastic cover slip may be applied to the sample and sealed in any of several ways. For instance, it is well known in the art to affix a cover slip by use of nail polish as an adhesive, or to attach the cover slip by surface tension of the sample liquid, and immerse the assembly of slide, sample, and cover slip in a bath of oil. Neither method is fast or convenient. Opening and resealing the reaction chambers requires considerable time and dexterity.

Presently, commercial products are available for sealing samples on microscope slides. One such product is a stiff plastic cover slip pre-affixed to a rubber gasket (Probe-Clip Incubation Chambers, Grace Bio-Labs, Inc., Pontiac Mich.). These are intended for sealing slides for in situ hybridization, and other similar techniques that involve high temperature incubations but do not involve thermal cycling. Because the cover slip of this device is relatively inflexible, thermal cycling will result in cyclic pressure changes within the chamber, leading to leaks. The rubber gasket of this device is relatively non-deformable, (approximately 30 durometer Shore A); thus it is not suited to sealing on rough or imperfectly clean surfaces. Because the cover slip and gasket are permanently joined, and because the cover slip is stiff, the cover slip can not be peeled away leaving the gasket behind. Therefore, reaction mixture must be applied to the slide-affixed sample by placing the reaction mixture on the cover-slip-gasket assembly and placing the inverted slide onto the assembly. This method is inconvenient and not suitable for automation.

Another such product is a molded-plastic funnel-shaped device with adhesive applied around the rim (Gene Cone chambers, Gene Tec Corporation, Durham N.C.). The wide mouth of the funnel is applied to the slide over the sample, fluid is added, and the mouth of the funnel is sealed with tape. These techniques are called sample contact methods because the sealing device, a cover slip or cone, contacts the reaction volume of the sample. In the prior art non-sample contact method, a seal is placed in contact with the reaction vessel so as to trap a volume of air inside the sample vessel above the reaction volume, assuming of course that the vessel is not completely full of liquid. The upper portion of the reaction vessel and the sealing device are maintained during the cycling process at a sufficiently high temperature so that water vapor will not condense inside the reaction vessel. Thus, while a small amount of evaporation occurs in the vessel during cycling, the vapor phase in the vessel becomes saturated with water vapor and no additional evaporation takes place. This method has the obvious advantage in that the sealing device does not touch the reaction volume, cross contamination of reactions is minimized or eliminated and the tedious task of removing oil from the top surface of liquid in each of the vessels is eliminated.

A problem associated with non-sample contact methods is, however, that such methods place stringent demands on the sealing device itself. As the air volume of the aqueous phase inside a sealed vessel is heated from room temperature to 95° C., more than 1 atmosphere of pressure will develop within the vessel from a combination of thermal expansion and the increase of the partial pressure of water. Although the temperature of the sealing device must be more than 100° C. and the internal vapor phase is saturated with water, the sealing device must endure repeated cycles of 0.5–1 atmosphere pressure change without leaking.

FIG. 1 illustrates the most common implementation of the non-sample contact sealing method. As shown in FIG. 1, a thermal cycler block 1 holds a multiplicity of reaction vessels in a XY matrix, although only two such reaction vessels, 2 and 3, are shown for purposes of illustration in FIG. 1. Within each of the reaction vessels 2 and 3, volumes of liquid 4 and 5 are contained within the interior of the vessel. The vessels 2 and 3 may be made of polypropylene or similar material and be of nominal 0.2 ml volume. Each of the vessels or test tubes is sealed by individual caps 6 and 7 shown in FIG. 1. Such caps, which may also be made of polypropylene, are well-known and are commercially available from Perkin-Elmer of Norwalk, Conn. and from Robbins Scientific of Sunnyvale, Calif.

The now capped tubes 2 and 3 are held upright in heating/cooling block 1 of a thermal cycling apparatus well known in the art. A flat plate 8 positioned above the caps applies pressure to assist in the sealing of the caps within the tubes as well as to provide heat to prevent water vapor condensation. The caps are usually tight-fitting to minimize leakage. There are certain disadvantages in terms of performance, convenience and cost of such caps. Because the caps must be made with a tight fit, they are difficult to insert and remove. For optimum function, the caps must be inserted using special tools. The force of removal can sometimes generate aerosols or splashing that may result in cross contamination of samples. The tubes are difficult to manufacture and relatively costly.

U.S. Pat. No. 5,123,477 to Tyler, issued May 23, 1992, illustrates, in FIG. 2 thereof, a reaction vessel and a sample chamber with a number of apertures 140 to contain a number of sample vials 62 as shown in FIG. 1 of the same patent. In addition, the specification of "GeneAmp PCR System 9600", available from Perkin-Elmer, shows, in FIG. 3 thereof, a vessel with an individual cap 2 inserted in the open mouth of the reaction vessel. In that same specification, a multi-vessel tray is illustrated.

An alternative non-sample-contact sealing method in the prior art is the use of an adhesive tape, such as that available from Excel Scientific of Phelan, Calif. Adhesive tape may be used either on 0.2 ml tubes as described above, or on thermal-formed 96 well microplates, such as those available from Nelipak Thermoforming of The Netherlands. For the adhesive tape to be useful, it must form a gas-tight seal around the mouths of thermal cycling vessels. The mouth surfaces are typically somewhat rough, and it is difficult to maintain that seal at the required temperature in view of the internal pressures within the vessel, the presence of water vapors, as well as the stresses placed on the vessels and the tape by cycling through a number of wide temperature variations. Commercial adhesive tapes typically cannot contain the required pressure without the application of an external force to maintain contact of the tape with the vessels. However, in a multi-vessel array, the height variations among the various components in a sealing system (a sealing system consists of the wells of the thermal cycler, the vessels themselves, the sealing device, and the device for applying pressure from above) typically amount to more than 0.1 mm, which is a typical thickness of a tape.

Thus, even with a source of pressure above the vessels, some vessels will have effectively no applied pressure from the plate because they are below the general plane of a number of the vessels. In addition, adhesive tape which runs across the open mouths of a number of vessels may adhere too tightly to the vessel mouths and cause, upon its removal, spilling and potential cross contamination of samples. Obviously, this is an undesirable effect. In addition, while the adhesive tape does allow for sealing without having to manipulate a multiplicity of caps of other prior art methods discussed above, the adhesive tape method has the disadvantages described above. Thus, there is a need in this field for a technique for sealing a number of vessels to both provide efficient sealing to compensate for differences in heights of test vessels and to eliminate the need for a multiplicity of sealing caps to be manipulated.

SUMMARY OF THE INVENTION

It is an object of the present invention to provide an apparatus which seals test vessels in an efficient manner throughout thermal cycling while allowing access to any or all of the vials without having to remove individual caps and without causing cross contamination of samples.

It is a further object of the present invention to provide a sealing device which seals despite the presence of variations in the heights of the top surfaces of the individual test vessels positioned within the thermal cycling device's rack or temperature control block.

It is also an object of the present invention to provide a sealing device which seals an aqueous sample on a glass microscope slide for thermal cycling applications in an efficient manner, while allowing opening and resealing of the sample area.

These objects are accomplished in the present invention through the use of a multilayer composite sheet material that can be used to simultaneously seal one or more vessels for thermal cycling and may comprise two layers: a backing layer to provide strength and a deformable layer to effect the seal and to compensate for variations in the height of the vessels to be sealed. In addition, the multilayer composite sheet material may have a removable release liner to protect the sealing layer during shipping and handling as well as to releasably form a barrier over the deformable layer to prevent it from sticking to surfaces until it is used in a thermal cycling device.

In a first embodiment, the backing layer may consist of any substance without great thermal resistance and with sufficient tensile strength so as not to fail at 1 atmosphere of pressure at 100° C. Examples include aluminum sheet, aluminum foil, polypropylene film, polyester film (DuPont Mylar), polyimide (DuPont Kapton), FEP fluorocarbon film (DuPont Teflon) and laminates of these and other materials. The sealing deformable layer is relatively thick, for example, between 0.1 mm and 1 mm, is deformable elastically or inelastically and has a tacky surface. Examples of suitable materials for the sealing layer include, but are not limited to, inelastically deformable uncured silicone rubber (available from General Electric and Dow-Corning) or elastically deformable silicone gel (available from Dow-Corning as product Sylgard). Sealing layers made from compositions of silicone, cured or uncured, containing compounds processed in ways to promote thermoconductivity, hardness, permeability or tack can be used as well within the scope of the present invention. The removable release liner can be of any material that is easily removed from the sealing layer, for example, polyethylene film.

In the manufacture of the multilayer composite sheet material of the first embodiment, the sealing material may be calendared or cast onto the backing layer. By suitably adjusting the thickness and hardness and surface tackiness of the sealing layer, a reliable seal can be formed with a wide variety of vessels while still allowing easy removale of the sealing sheet. The thickness of the sealing layer is important because it must be thick enough to compensate for the maximum expected height variation of the vessels positioned in the rack or temperature control block and all other components of the sealing systems. At the same time, it must not be so thick as to form an excessive thermal barrier or be excessively costly. Hardness must be adjusted so that the sealing layer will not be completely crushed by an applied force of 250 gf per vessel while conforming adequately to the vessels at an applied force of 50 gf per vessel. Surface tackiness is also important, with a peel strength of at least 0.1 gf/cm being preferred to form an adequate seal. Surface adhesiveness may be adjusted by varying the composition of the sealing layer, or by the application of adhesive compounds to either surface of the sealing layer. It has been found that a peel strength of more than 50 gf/cm can lead to problems with samples splashing during removal of the sealing layer. Adhesion of the sealing layer to the backing layer may be adjusted so that the backing layer may be removed from the sealing layer, and samples recovered by piercing the sealing layer.

In a second embodiment, the backing layer is relatively thin, for instance between 0.02 and 0.1 mm, and may consist of any substance with low permeability to water vapor and with sufficient tensile strength to maintain physical integrity at 100i C. It is preferred that the material be flexible for easy application to and removal from a surface, and transparent to light so that samples may be viewed without removal of the device. Example materials include polyester (DuPont Mylar), polyimide (Dupont Kapton), FEP fluorocarbon (Dupont Teflon), high density polyethylene, polypropylene, or laminates of these and other materials. The sealing layer is relatively thick, for instance between 0.05 mm and 0.5 mm, deformable either elastically or inelastically, and has a tacky surface. Suitable materials are similar to those for the first embodiment described above. The backing layer and sealing layer are formulated so that they will adhere to each other with a peel strength of no more than 50 gf/cm; the sealing layer adheres more tightly to glass than it does to the backing layer. The removable release liner can be of any material that is easily removed from the sealing layer, for example, polyethylene film.

In the second embodiment, devices under the invention are constructed by cutting the laminated material into suitable sizes, for instance a size adapted to fit onto a microscope slide, and removing one or more internal areas of the sealing layer. Devices according to the second embodiment are applied to a microscope slide or similar solid support with the sealing layer down, thus forming a chamber for the containment of sample. This sample chamber has a base comprising a microscope slide or similar solid support, a perimeter comprising the sealing layer, and a top comprising the backing layer. In normal use, the sample substantially fills the sample chamber. Thus, the second embodiment is a sample-contact sealing apparatus, and therefore little internal vapor pressure is generated. The small amount of pressure which may develop may be completely taken up by flexure of the backing layer, so that no external force is required to maintain the seal. During use, the sealing layer remains adhered to the base, while the backing layer can be removed and replaced multiple times to allow access to the sample for processing and analysis. Deformability of the sealing layer is a necessary feature so that very good seals may be formed with either the backing layer or the solid support, in spite of the presence of particulate matter or dried solutions, such as may accumulate during the processing of biological samples and reaction mixtures.

BRIEF DESCRIPTION OF THE DRAWINGS

Patentable features characteristic of the invention are set forth in the appended claims. The invention itself, however, as well as modes of use and further advantages, is best understood with reference to the following description of illustrative embodiments when read in conjunction with the accompanying drawings.

FIGS. 5(*a*) and 5(*b*) illustrate yet another embodiment of the present invention, in which a sealed chamber is formed on a microscope slide using the composite sheet material of the present invention.

DETAILED DESCRIPTION OF THE INVENTION

Figure 1:
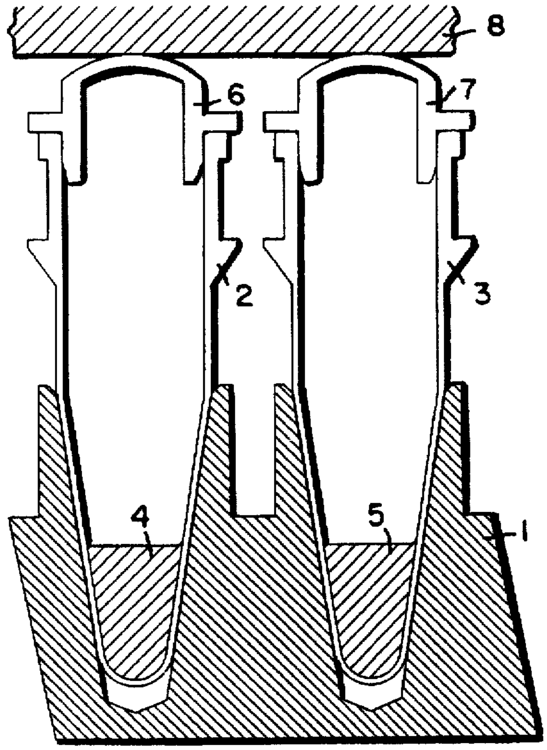
FIG. 1 PRIOR ART
FIG. 1 is a diagram showing a prior art arrangement of multiple vessels in a thermal cycling device.

Referring to FIG. 1 described above, the prior art method of providing an individual cap for each of the vials, the plate 8 positioned above the vials 2 and 3 has the dual purpose of applying pressure to the caps 6 and 7, as well as heating the upper sections of the thermal-cycling vessels so as to prevent condensation of water vapor within them.

Figure 2:
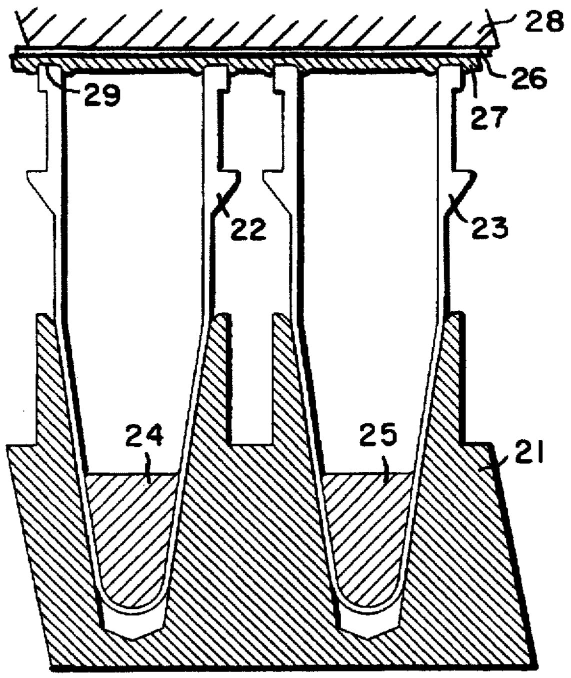
FIG. 2 illustrates the multilayer composite sheet material of the present invention within a thermal cycling device.

Referring to FIG. 2 which illustrates the use of the first embodiment of the multilayer composite sheet material of the present invention, a temperature control block 21 contains and maintains in an upright position a number of sample vessels 22 and 23. Each of the vessels 22 and 23 may contain a liquid sample 24 and 25. The temperature control block 21 forms a portion of a thermal cycling apparatus. The upper portion of the thermal cycling apparatus includes a flat, heated plate 28. Plate 28 conventionally has as its purpose both heating the upper sections of the thermal-cycling vessels 22 and 23 (so as to prevent condensation of water vapor within them), as well as providing a seal by pressing on the upper surface of a sealing device such as shown as caps 6 and 7 shown in FIG. 1. Between the lower surface of plate 28, and the open mouths of the vessels 22 and 23, is placed the multilayer composite sheet material 26, 27 of the present invention.

The material comprises two layers. A first layer 26 is in contact with the lower surface of plate 28. The layer 26 is described above as the backing layer and provides strength and uniformity to the sealing layer 27 to which it is adhesively bonded. Pressure and heat applied by plate 28 to the backing layer 26 is transmitted to the sealing layer 27. In a preferred embodiment, backing layer 26 is of a material described above, which is flexible to allow easy application and removal of the multilayer composite device, and easily punctured by a hypodermic needle to allow removal of reaction products from individual vessels without causing cross contamination between the contents of different vessels.

Deformable sealing layer 27 is illustrated in FIG. 2 at 29 as having been deformed by the pressure of the heating plate 28 to effectively seal the open mouth of the tube 22. In a preferred embodiment, the sealing layer 27 is made of an inelastically deformable material so that the degree deformation introduced into the sealing layer by the act of sealing can be used to indicate uniformity of the pressure applied to the sealing device. As shown in FIG. 2, the thickness of the sealing layer is sufficient to take up height differences between tubes within the matrix while still providing a gas-tight seal. The tackiness of the sealing layer 27 provides, in conjunction with its deformability, an excellent seal for the mouth of each of the vials in the matrix in the thermal cycling apparatus.

Figure 3:
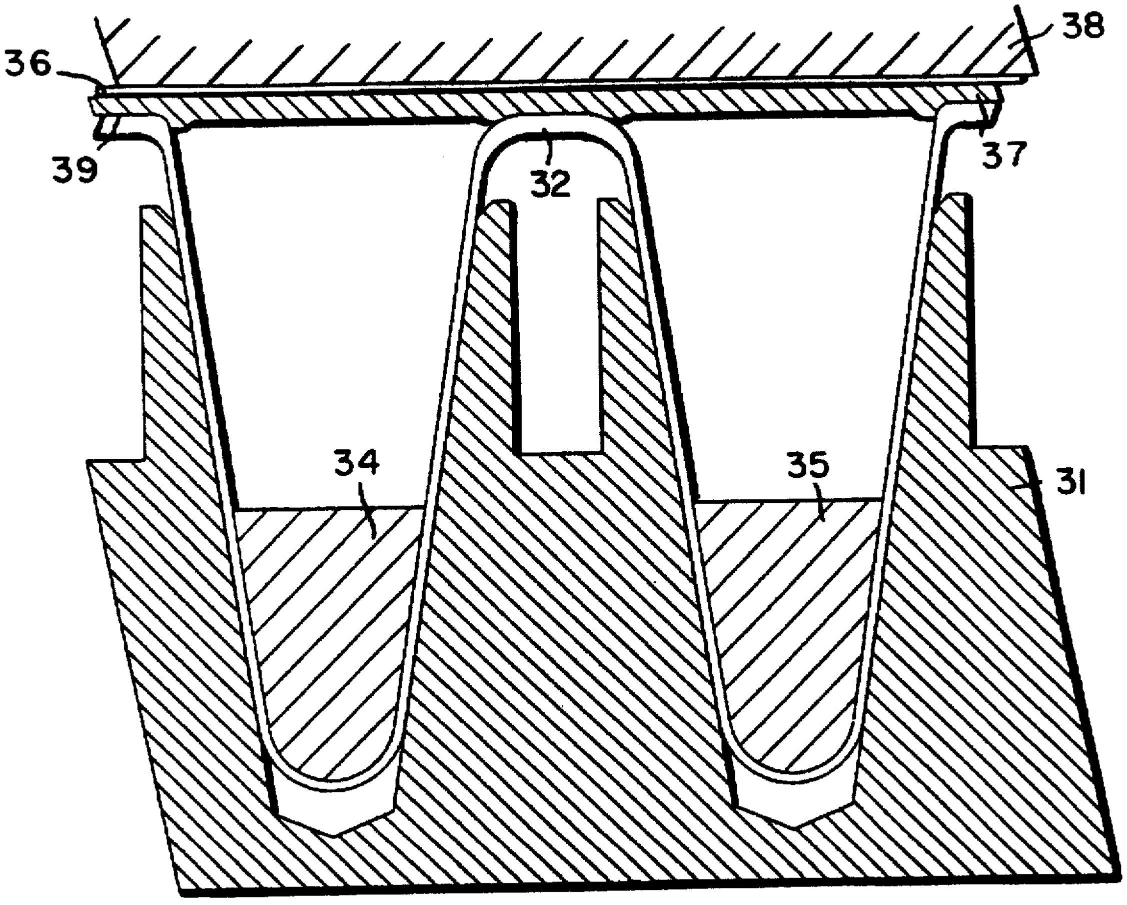
FIG. 3 illustrates another embodiment of the multilayer composite sheet material as applied to a second type of multi-well arrangement in a thermal cycling apparatus.

Referring to FIG. 3, another embodiment of the present invention is illustrated. In the device shown in FIG. 3, a temperature control block 31 matingly fits with a multiple well thermal cycling vessel, known as a microplate 32, which normally has 96 wells in an XY grid. However, for purposes of illustration, a 2-well section is shown, containing liquid samples 34 and 35. Above the microplate 32 is positioned a flat, heated plate 38, which as in the illustration of FIG. 2, provides pressure to seal the wells as well as providing heating to the upper sections of the microplate 32 so as to prevent condensation of water vapor within it. A multilayer composite sheet material 36, 37 is interposed between plate 38 and the top surfaces of the microplate 32. As in the embodiment of FIG. 2, the sheet material is comprised of two layers, a backing layer 36 and a sealing layer 37, which may be made of materials described above. When the composite sheet material of the present invention is placed on the upper surface of the microplate 32 and the flat, heated plate 38 placed over the composite sheet material, the sealing layer of the sheet material deforms as shown at 39 to conform to the shape of the top surface of the microplate 32, thus providing an effective seal for the contents of each well of the microplate.

Figure 4:
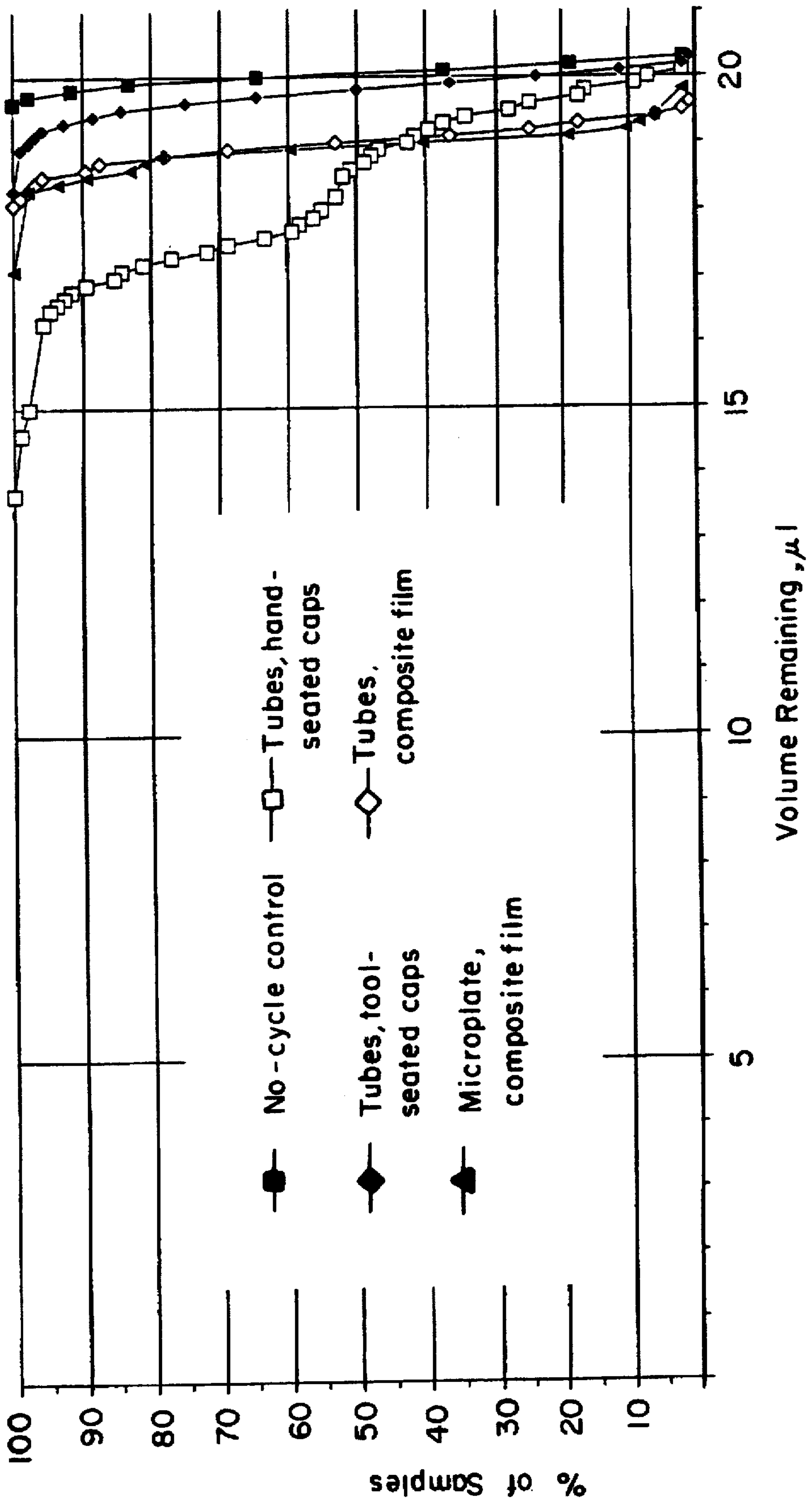
FIG. 4 is a chart which displays thermal cycling test results of the multilayer composite sheet material made in accordance with the present invention.

FIG. 4 is a chart which illustrates the results of sealing thermal cycling vessels with either caps of the prior art, such as those illustrated in FIG. 1 available from Robbins Scientific, or with a composite film constructed in accordance with the present invention, consisting in the examples used in connection with the chart of FIG. 4 of 0.04 mm polyester film backing and a 0.5 mm uncured silicone rubber sealing layer. Vessels were either 96 0.2 ml polypropylene tubes available from Robbins Scientific or a 96-well polycarbonate microplate available from Nelipak Thermoforming. The caps from Robbins Scientific were applied either by hand or with a cap-seating tool available from Perkin Elmer. A 20-microliter sample of distilled water with a small amount of tracer dye was placed in each tube or microplate well. Vessels were sealed, heated to 95° C. for two minutes then subjected to 20 cycles of 95° C. for 30 sec. and 40° C. for 30 sec. During cycling, a flat aluminum plate held at a temperature of approximately 115° C. applied approximately 5 kgf to capped or film-sealed tubes, or approximately 10 kgf to the film-sealed microplate. Water volumes remaining after 20 thermal cycles are graphed as the remaining volume versus the percentage of tubes containing at least that volume.

A control data set in which volumes remaining were measured without thermal cycling is displayed to validate measurement accuracy. These results illustrate that the losses of volume with a composite film sheet of the present invention are on average smaller and more consistent than are losses with hand-applied caps of the prior art, and only slightly greater than with tool-applied caps of the prior art. In addition, the composite film sheet of the present invention is capable of sealing a thermoformed microplate, a task which is not possible in the prior art. Thus, the multilayer composite sheet material of the present invention provides excellent sealing ability while providing the ability to be easily removed and replaced without causing cross contamination problems associated with prior art devices.

FIGS. 5(*a*) and 5(*b*) illustrate another embodiment of the present invention, but adapted for use with a microscope slide or similar device. The cross-sectional view of FIG. 5(*a*) shows the invention on the flat surface of a specially-adapted temperature control block 51, well known in the art. In the cross-sectional view of FIG. 5(*a*) as well as the oblique cut-away view, FIG. 5(*b*), the invention is applied to a glass microscope slide 52 with step surface 53.

In a sample-contact type sealing method, a liquid sample 54, is sealed onto the upper surface of the slide 52 for thermal cycling, by application of a multilayer composite sealing device 56, 57 to the slide 53. As in the embodiment of FIG. 2, the sheet material is comprised of two layers, a flexible backing layer 56 and a sealing layer 57, which may be made of any of the materials described above. The backing layer 56 in the embodiment FIGS. 5(*a*) and (*b*) is formed of a material that is flexible and relatively impermeable to water. A volume of material 55 is removed from the sealing layer 57 to provide a chamber for the liquid sample 54. Backing layer 56 may be removed, leaving sealing layer 57 adhered to slide surface 53, thereby forming an open-topped chamber for the acceptance of a sample. The backing layer 56 may then be reapplied to recreate a sealed chamber.

The present invention provides a simple but elegant solution for a problem which has been of concern to artisans in the field who wish to provide a device which both effectively seals and prevents cross contamination of individual samples in a multivial or multiwell set up. In addition, the multilayer composite sheet material can be constructed inexpensively enough to be discarded after use as one sheet, as opposed to a large number of caps or strips of tape.

Although this invention has been described in its preferred form with a certain degree of particularity, it is understood from the present disclosure that the preferred form has been made only by way of example and that numerous changes in the details of construction and the combination and arrangement of parts may be resorted as well as combination of functions within or as part of other devices, without departing from the spirit and scope of the invention as hereinafter claimed.

What is claimed is:

1. A multilayer composite material for contacting and sealing an open end of at least one reaction vessel wherein the reaction vessel has a closed end and an open end, comprising:

a first generally planar layer formed of a deformable material for contact with the open end of the at least one reaction vessel;

a second generally planar layer formed of a material which provides support to the first layer;

the first and the second layers being joined together to form a multilayer composite; wherein the first-mentioned layer is constructed of a material with hardness less than 30 Shore A and possesses a tacky surface on each side of the planar layer having a peel strength or polypropylene of at least 0.1 gf/cm but no more than 50 gf/cm.

2. The multilayer material of claim 1 wherein the first-mentioned material will maintain its integrity up to an applied force of approximately 100 gf/sq. cm.

3. The multilayer material of claim 1 wherein the first-mentioned material is comprised of a material which is inelastically deformable.

4. The multilayer material of claim 1 wherein the first-mentioned material is comprised of a material which is elastically deformable.

5. The multilayer material of claim 1 wherein the first-mentioned layer is between approximately 0.05 mm and 1.0 mm in thickness.

6. The multilayer material of claim 1 wherein the first-mentioned layer is comprised of an uncured silicone compound.

7. The multilayer material of claim 1 wherein the first-mentioned layer is comprised of a silicone gel.

8. The multilayer material of claim 1 wherein the first-mentioned layer contains internal gaps formed therein.

9. The multilayer material of claim 1 wherein the second-mentioned layer is comprised of a material which maintains its integrity at 1 atmosphere of pressure and 100 degrees temperature C.

10. The multilayer material of claim 1 wherein the second-mentioned layer is comprised of a material which is essentially impermeable to water.

11. The multilayer material of claim 1 wherein the second-mentioned layer is comprised of a material which is flexible.

12. The multilayer material of claim 1 wherein the second-mentioned layer is formed from a polyester film.

13. The multilayer material of claim 1 wherein the second-mentioned layer is between approximately 0.03 mm to 0.1 mm in thickness.

14. In an apparatus for thermally cycling reaction materials contained in at least one reaction vessel, the at least one reaction vessel having a closed end and an open end, the apparatus further including a temperature control block for supporting the at least one reaction vessel at its closed end, a flat heated plate disposed above the open end of the at least one reaction vessel, wherein the improvement comprises a multilayer composite material for sealing the open end of reaction vessels having:

a first generally planar layer formed of a deformable material for contact with the open end of a reaction vessel, a second generally planar layer formed of a material which provides support to the first layer, the first and the second layers being joined together to form a unitary multilayer composite, wherein in the first-mentioned layer is constructed of a material with hardness less than 30 Shore A and possess a tacky surface having a peel strength or polypropylene of at least 0.1 gf/cm on each side of the planar layer but no more than 50 gf/cm;

the multilayer composite being disposed between the flat heated plate and the open end of the at least one reaction vessel;

the first mentioned layer being deformed and sealing the open end of the at least one reaction vessel when the deformable surface of the composite is compressed onto the open end by the flat heated plate.

* * * * *

UNITED STATES PATENT AND TRADEMARK OFFICE
CERTIFICATE OF CORRECTION

PATENT NO : 5,721,136

DATED : February 24, 1998

INVENTOR(S) : Finney et al.

It is certified that error appears in the above-identified patent and that said Letters Patent is hereby corrected as shown below:

In Claim 1:

Line 62, delete the word "each" and add therein -- the --.

Line 62, insert after "planar layer" -- which contacts the open end of the at least one reaction vessel and --.

In Claim 14:

Line 20, delete the word "each" and add therein -- the --.

Line 20, insert after "planar layer" -- which contacts the open end of the at least one reaction vessel --.

Signed and Sealed this

Fourteenth Day of July, 1998

Attest:

BRUCE LEHMAN

*Attesting Officer* *Commissioner of Patents and Trademarks*